United States Patent
Foster et al.

(10) Patent No.: US 10,550,480 B2
(45) Date of Patent: Feb. 4, 2020

(54) METHOD AND SYSTEM FOR ION BEAM DELAYERING OF A SAMPLE AND CONTROL THEREOF

(71) Applicant: TECHINSIGHTS INC., Ottawa (CA)

(72) Inventors: Robert K. Foster, Dunrobin (CA); Christopher Pawlowicz, Ottawa (CA); Jason Abt, Kanata (CA); Ian Jones, Ottawa (CA); Heinz Josef Nentwich, Ottawa (CA)

(73) Assignee: TECHINSIGHTS INC., Ottawa, Ontario (CA)

( * ) Notice: Subject to any disclaimer, the term of this patent is extended or adjusted under 35 U.S.C. 154(b) by 460 days.

(21) Appl. No.: 15/378,551

(22) Filed: Dec. 14, 2016

(65) Prior Publication Data

US 2017/0096741 A1    Apr. 6, 2017

Related U.S. Application Data (62) Division of application No. 13/673,055, filed on Nov. 9, 2012, now Pat. No. 9,534,299.

(60) Provisional application No. 61/558,418, filed on Nov. 10, 2011.

(51) Int. Cl.
*C23F 4/00* (2006.01)
*G01N 1/32* (2006.01)
(Continued)

(52) U.S. Cl.
CPC ............. *C23F 4/00* (2013.01); *G01N 1/32* (2013.01); *H01J 37/32935* (2013.01);
(Continued)

(58) Field of Classification Search
CPC ........ C23F 4/00; G01N 1/32; H01J 37/32935; H01J 37/32963; H01L 21/2633; H01L 22/26; H01L 23/00; H01L 2924/0002
(Continued)

(56) References Cited

U.S. PATENT DOCUMENTS 5,438,747 A    8/1995   Krounbi et al.
6,288,393 B1 *  9/2001   Phaneuf ................. G01N 23/04
                                                        250/307
(Continued)

FOREIGN PATENT DOCUMENTS

CN    1122496 A    5/1996
CN    1190482 A    8/1998

OTHER PUBLICATIONS

Canadian Intellectual Property Office, Office Action for CA Application No. 2,791,249 dated Feb. 2, 2013, 3 pages.
(Continued)

*Primary Examiner* — Rodney G McDonald
(74) *Attorney, Agent, or Firm* — Knobbe, Martens, Olson & Bear, LLP (57) ABSTRACT

There is provided a method, system and computer program product to delayer a layer of a sample, the layer comprising one or more materials, in an ion beam mill by adjusting one or more operating parameters of the ion beam mill and selectively removing each of the one or more materials at their respective predetermined rates. There is also provided a method and system for obtaining rate of removal of a material from a sample in an ion beam mill.

12 Claims, 5 Drawing Sheets

(51) Int. Cl.
  *H01L 23/00* (2006.01)
  *H01J 37/32* (2006.01)
  *H01L 21/263* (2006.01)
  *H01L 21/66* (2006.01)
(52) U.S. Cl.
  CPC .... *H01J 37/32963* (2013.01); *H01L 21/2633* (2013.01); *H01L 22/26* (2013.01); *H01L 23/00* (2013.01); *H01L 2924/0002* (2013.01)
(58) Field of Classification Search
  USPC ........................................ 204/192.34, 298.36
  See application file for complete search history.

(56) References Cited

U.S. PATENT DOCUMENTS

| | | |
|---|---|---|
| 2002/0027746 A1 | 3/2002 | Okawa et al. |
| 2003/0084409 A1 | 5/2003 | Abt et al. |
| 2005/0285106 A1 | 12/2005 | Kane et al. |
| 2008/0078750 A1 | 4/2008 | Boguslaysky et al. |

OTHER PUBLICATIONS

Canadian Intellectual Property Office, Office Action for CA Application No. 2,791,249 dated Jun. 25, 2013, 2 pages.
Canadian Intellectual Property Office, Notice of Allowance for CA Application No. 2,791,249 dated Nov. 22, 2013, 1 page.
Crockett, et al. 2004 "Plasma delayering of integrated circuits" *MicroelectronicsFailsure Analysis Desk Reference* 4: 243-25.
Torrance, et al. 2011 "The state-of-the-art in semiconductor reverse engineering" *Design Automation Conference (DAC)*: 333-338.
Vyatkin, et al. 2010 "Integrated circuit failure analysis using physical ion sputtering" *Instruments and Experimental Techniques* 54.2: 268-272.

* cited by examiner

METHOD AND SYSTEM FOR ION BEAM DELAYERING OF A SAMPLE AND CONTROL THEREOF

CROSS-REFERENCE TO RELATED APPLICATIONS

This application is a divisional of U.S. patent application Ser. No. 13/673,055, filed Nov. 9, 2011, which claims the benefit of U.S. Provisional Patent Application No. 61/558,418, filed Nov. 10, 2011, each of which are hereby incorporated herein by reference in their entirety.

FIELD OF THE INVENTION

The present disclosure relates generally to delayering samples using ion beam mills, and in particular, using broad ion beam mills to delayer a layer of a sample, by selectively removing one or more materials of said layer, and control thereof.

BACKGROUND OF THE INVENTION

Removing a layer in a sample such as a semiconductor die involves removing very small amounts and very thin layers of an integrated circuit, which contains metals and dielectrics, to reveal the underlying circuitry in a precise and controlled manner. Typical methods include wet chemical etching, dry (plasma) etching, and mechanical polishing or physical abrasion.

Mechanical polishing is performed by manually polishing the sample using polishing pads and abrasive slurries to erode the surface of the sample to the extent needed. The problem faced during this process is the uneven erosion of the periphery and surface, wherein for example, copper is removed slower than $SiO_2$. This leads to the non-uniform removal of a given surface, due to various levels of stress exerted in different spots, or variations in feature density of the sample during labouring the sample.

Wet (chemical) etching is performed by using chemicals and immersing a sample into the chemical to cause a chemical reaction to remove material from the sample surface. This is very difficult to control as the rates at which the chemicals etch the various materials in the sample vary, and material interfaces can be severely affected, which once again leads to the non-uniform removal of materials.

Dry (plasma) etching is performed by using combinations of non-reactive gasses and/or reactive gasses, ionized under vacuum in a strong electric field. Reactive ions cause both chemical reactions on a sample and physical bombardment, thereby removing material from the sample, whereas non-reactive ions cause only physical bombardment of the sample and thereby eroding (knocking-off) the sample. The non-uniformities in material density and etch species concentration adversely affect the etch rate and subsequent removal processes.

Ion beam milling is also used for material removal in samples by etching or milling a sample. Ion beam mills may be used for various other purposes in the semiconductor industry, such as film deposition or surface modification or activation. Using an ion beam source with both reactive and non-reactive gases, the source gas is ionized and the positive ions are extracted and accelerated toward the sample residing on a rotatable cooled stage in a vacuum chamber. The angle of the sample stage can be adjusted for the desired impact of the ions on the surface of the sample. There are various Ion Milling systems known in the art, such as Focussed Ion Beam Milling (FIB) systems and Broad Ion Beam Milling (BIB) systems.

Very narrow (small diameter) ion beams, typically with gallium ions, are used in FIB systems to remove material in precise locations in a sample (often on semiconductor integrated circuits) and also to deposit new materials on the ICs. This is used to edit the circuits, rerouting connections to repair damage or introduce new functionality. FIB systems are also used to cross section samples, build novel physical structures, and physically shape material (micromachining) on a very small scale. A typical area shaped by the ion beam would be measured in microns, or at most, tens of microns. The sample is kept stationary, while the ion beam is scanned back and forth. Beam to sample angle can be controlled by tilting the sample. The target areas capable of being practically modified by FIB are restricted to small, due to the relatively slow milling rate of FIB systems. In addition, there are a number of other aspects relating to a small scanned beam that make it quite difficult to accurately modify large areas, including dwell time, overlap area, proximity between scans and features, that are all exacerbated as, for example, the very narrow beam is passed over the entire surface of a sample (such as an integrated circuit).

Medium diameter ion beams (millimeter sized) are typically used to 'clean up' a sample, removing surface damage generated in previous steps. One example is during transmission electron microscopy (TEM) sample preparation; a sample is polished using physical abrasives until it is very thin, then a medium diameter ion beam (often using Argon ions) is used to abrade the surface and gently mill away a thin layer (of nanometers thickness). The beam is kept stationary while the sample is typically rotated or scanned back and forth, or both. Beam to sample angle is usually adjustable by moving the ion gun. Milled area is measured in hundreds of microns, or in millimeters.

Finally, broad ion beam milling systems (centimeters in diameter) are also used in the fabrication process of semiconductor devices. A layer of a sample is masked, when the sample is exposed to the beam, material is removed over a large area where not protected by the mask. The gun is stationary but the sample can be rotated and tilted to different angles. Milled area is measured in centimeters. The material removed is typically homogenous in nature (a layer of a single material or single compound is milled until removed). BIB mills have been limited to removing a layer of homogenous material as the removal rate is maintained constant for a given homogenous layer until the next layer is reached. BIBmilling ion guns are associated with "grids" or "fields" in front of the ion gun that are capable of changing parameters of the beam. Typical beam spreads in broad beam ion gun applications are in the range of 5 to 20 cm. Typically, broad ion beam applications in Integrated Circuits (IC) include deposition and de-layering when building structures on an IC.

In deposition applications, broad ion beams are directed at a material source. The ion beam bombards the material source and causes the atoms of the material source to be ejected therefrom. A substrate is placed in a location where the ejected material source will hit and bond as a layer thereto in a more or less even fashion. The substrate can be moved linearly (in x, y and z directions) and rotated (about x, y and z axes—which would include a change in tilt angle of the substrate, relative to the main [?] direction of impact of the ejected material source). A mask can be used to create pre-defined structures on the substrate. Alternatively, material can be deposited on the mask beforehand in a predefined pattern that, when removed, causes the deposited material to remain on the substrate in a negative image of the predefined pattern.

In material removal applications, broad ion beams are directed at a sample in order to remove sample material in a non-selective manner. Generally, when a mask is pre-applied to the sample or a masking material is deposited on the sample beforehand in a predefined pattern. Known systems are directed to unselectively remove homogenous material layers of the sample without eroding the mask or the sample under the mask to facilitate creation of structures on an IC. The angle of the sample may be adjusted to maximize the removal rates for a substantially homogenous material layer. An endpoint detection system may also be used to detect when the substantially homogenous material layer has been substantially removed and the material from a subsequent layer is being removed, at which point removal is stopped.

U.S. patent application Ser. No. 11/205,522, discloses a "Method of Reworking Structures Incorporating Low-K Dielectric Materials". U.S. patent application Ser. No. 11/661,201 discloses "Directed Mult-Deflected Ion Beam Milling of a work Piece and Determining and Controlling Extent Thereof". Further, U.S. Pat. No. 5,926,688 discloses "Method of Removing Thin Film Layers of a Semiconductor Component". However, none of the noted patent or patents overcomes the shortcomings in the general area of delayering a sample.

Therefore there is a need for a method and system to overcome some of the shortcomings in the general area of delayering a sample.

This background information is provided to reveal information believed by the applicant to be of possible relevance to the present technology. No admission is necessarily intended, nor should be construed, that any of the preceding information constitutes prior art against the present invention.

SUMMARY OF THE INVENTION

An object of the present technology is to provide a method and system for ion beam delayering of a sample and control thereof.

In accordance with an aspect of the present technology there is provided a method of delayering a layer of a sample using an ion beam mill, wherein the layer comprises one or more materials, the method comprising: placing the sample in the ion beam mill; operating the ion beam mill; adjusting one or more operating characteristics of the ion beam mill; and selectively removing each of the one or more materials at respective predetermined rates.

In accordance with another aspect of the present technology there is provided a method of delayering a sample, the method comprising: providing a broad ion beam mill; placing the sample inside a processing chamber of said ion beam mill; controlling said ion beam mill; and selectively removing one or more materials in a layer of said sample.

In accordance with another aspect of the present technology there is provided a system for delayering a layer of a sample, wherein the layer comprises one or more materials, the system comprising: an ion beam mill; and a control system in operative communication with said ion beam mill to control one or more operating characteristics of the ion beam mill to selectively remove each of the one or more materials at respective predetermined rates.

In accordance with another aspect of the present technology there is provided a system for delayering a sample, the system comprising: a broad ion beam mill; and a control system in operative communication with said broad ion beam mill, wherein said control system controls said broad ion beam mill to selectively remove one or more materials in a layer of said sample placed inside a processing chamber of said broad ion beam mill.

In accordance with another aspect of the present technology there is provided a computer program product for delayering a layer of a sample, wherein the layer comprises one or more materials, the computer program product comprising code which, when loaded into memory and executed on one or more processors, is adapted to control a system, said system comprising an ion beam mill, to selectively remove each of the one or more materials at respective predetermined rates.

In accordance with another aspect of the present technology there is provided a computer program product for delayering a sample, the computer program product comprising code which, when loaded into memory and executed on one or more processors, is adapted to control a system, said system comprising a broad ion beam mill, to selectively remove one or more materials in a layer of said sample placed inside a processing chamber of said broad ion beam mill.

In accordance with another aspect of the present technology, there is disclosed method of reverse engineering a sample using an ion beam mill, wherein the sample comprises one or more materials, the method comprising the steps of placing the sample in the ion beam mill; operating the ion beam mill; adjusting one or more operational characteristics of the ion beam mill to selectively remove each of the one or more materials at respective predetermined rate; removing a layer of constant thickness from a top surface of the sample; and acquiring surface data from the top surface of the sample. The surface data may comprise a picture, image or other data representation capable of characterizing the features or other aspects of the top surface. The method may optionally be performed wherein the step of removing the layer of constant thickness is achieved in a single step, wherein the predetermined rate of removal for each material present in the layer of constant thickness is the same, or it is repeated multiple times, wherein each repeat the respective rate of removal for each material may be different but the result of the repeated steps, each with the ion beam mill at different operating characteristics, results in removing a layer of constant thickness. Optionally, the method may further comprise the step of repeating the aforementioned steps until either a predetermined number of layers or predetermined total thickness of the sample, both as predetermined by the operator, have been removed from the sample. Optionally, the method may further comprise the step of producing hierarchical circuit schematics using the acquired surface data from each removed layer.

BRIEF DESCRIPTION OF THE DRAWINGS

Features and advantages of the present technology will become apparent from the following detailed description, taken in combination with the appended drawings, in which.

DETAILED DESCRIPTION OF THE INVENTION

Definitions:

Sample: A sample may refer to a composition of one or more materials. A sample may also refer to, but is not limited to: a semiconductor device, Integrated Circuit, a layer of metals and dielectrics of any thickness, one or more materials in an area of any size, optical devices, electronic devices, or any combinations thereof. A worker skilled in the art would readily understand the meaning of a sample for the purposes of the subject matter disclosed herein.

Delayering may entail, but is not limited to: removal of one or more layers, partly or wholly, wherein the one or more layers or portions thereof may comprise one or more materials; removal of one or more layers, partly or wholly, comprising one or more materials, wherein the one or more layers may comprise small or large surface areas; removal of one or more layers, partly or wholly, wherein the one or more layers may be of any desired thickness; removal of one or more materials, partly or wholly, to any extent desired; removal of one or more substantially parallel layers, partly or wholly, wherein the one or more substantially parallel layers layers or portions thereof may comprise one or more materials; removal of one or more substantially planar layers, partly or wholly, wherein the one or more substantially planar layers or portions thereof may comprise one or more materials; removal of one or more substantially constant thickness parallel layers, partly or wholly, wherein the one or more substantially constant thickness parallel layers or portions thereof may comprise one or more materials; removal of one or more varying thickness parallel layers, partly or wholly, wherein the one or more varying thickness parallel layers or portions thereof may comprise one or more materials or any combinations thereof. For the purposes of the subject matter disclosed herein, the terms delayering and de-layering may be used interchangeably.

Homogenous, for the purposes of this disclosure, it is used to describe materials, structures, compositions or portions thereof, which comprise solely one material.

Non-Homogenous, for the purposes of this disclosure, it is used to describe materials, structures, compositions or portions thereof, which comprise more than one material.

As used herein, the term "about" refers to a +/−10% variation from the nominal value. It is to be understood that such a variation is always included in a given value provided herein, whether or not it is specifically referred to.

Unless defined otherwise, all technical and scientific terms used herein have the same meaning as commonly understood by a worker of ordinary skill in the art to which this invention pertains.

In the instant application there is provided a method, system and computer program product to delayer a layer of a sample, the layer comprising one or more materials, in an ion beam mill by adjusting one or more operating parameters of the ion beam mill and selectively removing each of the one or more materials at their respective predetermined rates.

Figure 1:
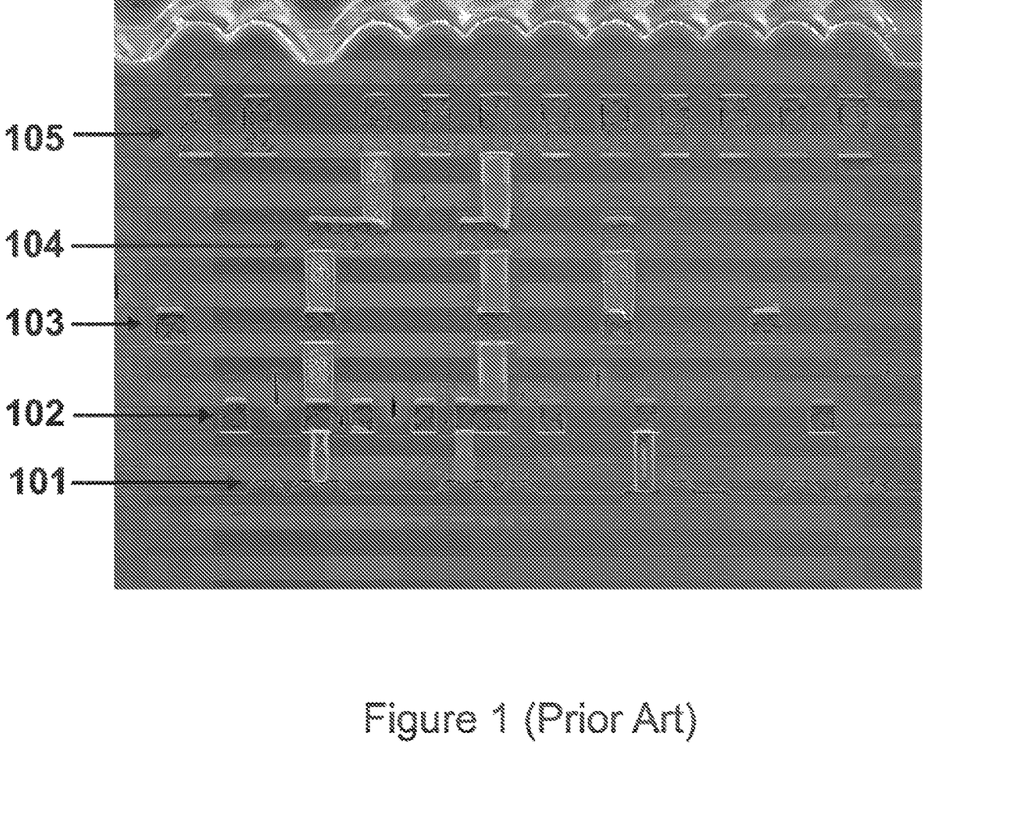
FIG. 1, in aspects, is a representation of the various layers that may be present in an IC (Prior Art).

Delayering a sample in an Ion Beam Mill:

Delayering may be done using various ion beam mills, such as FIB mills or BIB mills. In aspects of the subject matter disclosed herein, delayering of a sample is performed in a BIB mill. An ion beam mill may be used to remove one or more layers of an IC, layer by layer, to expose the underlying circuitry across the entire surface of the IC. For example, as seen in FIG. 1, an IC may have many layers. The bottom most layer may be a poly layer 101. Following the poly layer may be a number of metal layers 102 to 105. A worker skilled in the art would readily understand the layers within an IC.

According to some embodiments of the invention, a layer of a sample or portions thereof may be made up of one or more materials. Removal of a layer may comprise, partly or wholly, removing one or more materials resident within. A layer may be of any thickness. One or more materials present in a sample may be any one or more materials from the chemical periodic table. Each layer may be made up of a mixture of materials such as, but is not limited to, metals and dielectrics in varying shapes and structures. There are a wide number of ion beam mills readily available in the market as would be known to a worker skilled in the art. For the purposes of this disclosure, ion beam mill, mill and ion mill may all be used interchangeably. Similarly, Broad Ion Beam mill, BIB mill and Broad Beam Ion mill may all be used interchangeably.

Figure 2:
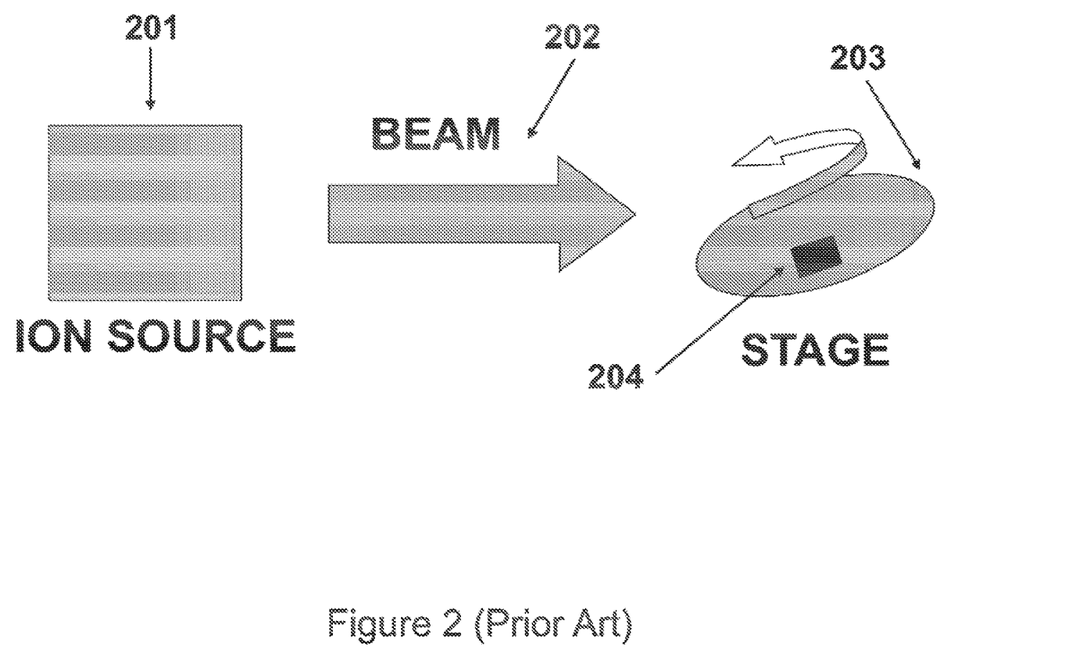
FIG. 2, in aspects, is a representation of an ion gun, ion beam, sample stage and a sample (Prior Art).

An ion beam mill may consist of one or more ion beam sources. According to some embodiments of the invention, the ion mill consists of one or more large diameter gridded ion beam source and a, variable angle, cooled sample stage that can be tilted and rotated. A sample stage may be housed in a vacuum chamber. Various gas injection systems may deliver different process gasses, while a plasma bridge neutralizer may be used to neutralize the ion beam. Vacuum gauges, a load-lock, vacuum pumps, one or more control panels, and one or more processors may also be associated with the ion mill. The ion mill may also comprise elements to introduce various gasses and one or more elements to control the sample stage. Furthermore, one or more ion beam sources may be associated with apertures and electrostatic lenses. The ion mill may consist of one or more actuators to actuate one or more elements of the ion mill. The ion mill may comprise one or more controllers or a control system comprising one or more processors to control the one or more ion mill operating characteristics or parameters. It is to be understood that the operation of an ion mill and the various fundamental components of an ion mill would be readily known to a worker skilled in the art. FIG. 2 shows illustrative example of an ion source 201 from which an ion beam 202 is produced. The ion beam impinges on a sample 204, which is placed on a sample stage 203.

According to some embodiments of the invention, the ion mill and its various components may be collectively referred to as the ion mill. The ion mill may comprise an end point detection unit as one of its components. The end point detection unit may be in operative connection with the ion mill. The end point detection unit may be capable of detecting or measuring one or more changes in the sample as one or more materials are being removed. For example, the detection unit may detect or measure the existence and/or quantity of different materials. The ion mill may comprise an imaging system as one of its components. The imaging system may be in operative connection with the ion mill. A worker skilled in the art would readily know various end point detection units and imaging systems. Furthermore, the ion mill together with a control system may form a system to delayer a sample.

Generally, delayering a sample in an ion beam mill involves an ion beam incident and impinging upon a surface of the sample whereby interaction of the ion beam with the surface results in removal of material from the surface at a rate. For the purposes of the subject matter disclosed herein, the terms rate, material removal rate, removal rate, delayering rate, milling rate, etch or etching rate, material rate, and rate of removal may all be used interchangeably.

The surface of the sample may be non-homogenous and therefore constitutes different compositions of materials. The surface of the sample may also be homogenous, which constitutes a single material composition. The removal of material from the surface may be via selectively removing one or more of the materials resident on the surface. The removal of material from the surface may be via non-selectively removing one or more materials without having any control over which material is being removed from the surface. Upon delayering a surface of a sample, the underlying surface may be left substantially uniform or even regardless of the delayered surface being homogenous or non-homogenous. Upon delayering a surface of a sample, the underlying surface may also be left substantially non-uniform or uneven.

According to some embodiments of the invention, the ion beam mill is configured by adjusting one or more of its operating characteristics. The one or more ion beam mill operating characteristics may be associated with a predetermined rate at which a material may be removed. Delayering a sample may be achieved by configuring the ion mill to remove one or more materials from the sample at their respective predetermined rates. The association of rates of removal to sets of ion mill operating characteristics may be obtained experimentally through trial and error or via simulation methods. The rates of removal and their associated sets of ion mill operating characteristics may be logged or stored for future manipulation of the ion mill in any storage medium such as a database, memory device, computing storage device or any storage medium as would be known to a worker skilled in the art.

Delayering may be set to take place for a certain time; after which, the sample may be removed from the ion beam mill, analyzed, and further delayering necessitated, until the desired level of delayering is achieved.

According to some embodiments of the invention, delayering may be set to take place until a certain thickness of the sample is delayered. Delayering may also involve removal of substantially parallel homogenous or non-homogenous layers. The surface area of the layer of the sample to be delayered may be large. Furthermore, the surface area of the layer of the sample to be delayered may be in the range of 5 to 20 square centimetres.

According to some embodiments of the invention, a Secondary Ion Mass Spectroscopy (SIMS) end point detection unit may be used to help with accurately controlling milling rates. A worker skilled in the art would readily understand SIMS and its usage as an end point detection element. Visual detection, chemical detection tools, other mass spectroscopy tools or any end point detection system as would be readily known to a worker skilled in the art may also be used as an end point detection unit/element to accurately control milling rates.

According to some embodiments of the invention delayering may be performed for reverse engineering the circuitry inherent within a device. An ion beam mill may be used to delayer a device layer by layer and exposing the circuitry or circuit connections on the surface of each layer. Upon delayering the device, pictures, images or other representation (e.g. circuit schematic model based on data representative of detected surface features) may be taken of each layer, thereby, capturing the circuitry or circuit connections on the surface of each layer. By piecing together the pictures, images, or other representations of the different layers, using appropriate software tools, circuit connections between the various components that may be inherent within a device, both across and between layers, can be produced. The process may be repeated for various devices within a larger device and a hierarchical schematic of the circuit connections of the various devices within the larger device may be developed. Proprietary software tools may also be used to produce hierarchical circuit schematics. Such circuit schematics may be useful in identifying evidence of use of claim elements in the target device being delayered. According to some embodiments of the invention, delayering may be performed for, but is not limited to, failure analysis (defect identification), circuit edit, sample/device characteristics measurement, verification of design, and counterfeit detection.

Selectivity:

The operation of an ion beam mill, as mentioned above, may depend on one or more ion beam mill operating characteristics or parameters. The operation of an ion beam mill and the results of such operation may vary based on the adjustments made to one or more ion beam mill operating characteristics.

According to some embodiments of the invention, the one or more ion mill operating characteristics or parameters may include, but are not limited to, ion beam direction, ion beam size, sample cooling, chamber base pressure, chamber cross-over pressure, chamber process pressure, load lock base pressure, load lock cross-over pressure, sample stage linear location, sample stage angle, sample stage rotation speed, sample stage temperature, ion source accelerator voltage, ion source accelerator current, ion source beam voltage, ion source beam current, ion source extractor grid configuration, ion source extractor grid material, plasma bridge neutralizer (PBN) cathode voltage, plasma bridge neutralizer emission current, PBN gas flow, ion source gas flows and types, background gas flows and types, angle of sample-to-ion gun, any chamber condition, and sidewall angle or any combinations thereof or any ion mill characteristic or parameter that may be adjusted as would be known to a worker skilled in the art. For the purposes of the subject matter disclosed herein, ion mill operating characteristics, ion mill operating parameters, characteristics, and parameters may be used interchangeably. Similarly, sample stage angle and sample angle may be used interchangeably. Beam angle, sample to beam angle or sample stage to beam angle would all mean the angle at which the beam impinges on the sample.

According to some embodiments of the invention, the ion source radio frequency power may be forward or reflected. The ion source extractor grid configuration may include selecting the appropriate material, size, number and grid pattern of the extractor grids. The extractor grid configuration may be set to produce focussed, collimated or divergent beam. According to some embodiments of the invention the ion source gas flows and types may be multiple. The ion source gas may be inert or reactive. Furthermore, the background gas flows and types may be multiple. The background gas may be reactive. In addition, the angle of sample-to-ion gun may be adjusted by moving either the sample stage or ion gun or both. The angle of sample-to-ion gun may be adjusted to select optimum etching/milling rates. According to some embodiments of the invention, the ion source extractor grid material may be graphite, molybdenum or any other material as would be readily understood by a worker skilled in the art.

According to some embodiments of the invention, adjusting the one or more ion mill operating characteristics may provide different material removal rates. For example, for a given set of ion mill operating characteristics the rate of removal for a particular material in a particular sample or different samples may be the same. As another example, a given material in a given sample may have different rates of removal for different sets of ion mill operating characteristics. As a further example, a given material in different samples may have different rates of removal for a given set of ion mill operating characteristics. As yet another example, a given material in different samples may have different rates of removal for different sets of ion mill operating characteristics. Various permutations and combinations of the one or more ion mill operating characteristics may provide different rates of removal for a given material in the same sample or in different samples. A set of ion mill operating characteristics or parameters may entail a set of values corresponding to the one or more ion mill operating characteristics or parameters associated to the rate at which a material may be removed.

According to some embodiments of the invention, the rate may be predetermined. Predetermined rates may be obtained through trial and error via experiments or via simulation methods. For a given material, the predetermined rate may be obtained by setting the ion beam mill characteristics to a certain set of values and obtaining the corresponding rate at which the material may be removed.

For example, a first predetermined rate for a particular material may be obtained by placing the material inside the ion mill and adjusting the operating characteristics to a certain set of values and logging the rate at which the material is removed. A second predetermined rate of removal for the same material may be obtained by adjusting the ion mill operating parameters to a second set of values. Furthermore, various sets of ion mill operating characteristics, for a given material, may be set and the corresponding rates determined. In addition, various combinations of ion mill operating characteristics may be set and experiments performed to obtain removal rates of one or more materials in the same or different samples. Rates determined as such may then be classified as predetermined rates. Predetermined rates may also be obtained via simulation methods. In aspects, predetermined rates of materials may be obtained by introducing reactive species and mixing them with matter ejected from the ion beam source. It is to be understood that any method of obtaining or measuring material removal rates would fall under the purview of this disclosure.

Predetermined rates for different materials may be associated with their respective sets of ion mill operating characteristics. The predetermined rates for different materials and their associated respective sets of ion mill operating characteristics may be logged manually or stored in any medium and used for future manipulation of the ion mill. According to some embodiments of the invention, each set of ion mill operating characteristics may comprise one or more ion mill operating characteristics. The values for the one or more ion mill operating characteristics within each set may be the values that would have been set during the trial and error or simulation process. In addition, as these values may be set during the trial and error or simulation process, they may also be regarded as predetermined values. Furthermore, the medium used for storage of sets of ion mill operating characteristics and associated respective predetermined rates is a computer drive, electronic device, optical device, or any storage medium that would be readily known to a worker skilled in the art. The storage medium may be part of the ion mill and the storage medium may be part of a system comprising the ion mill and a control system.

According to some embodiments of the invention, selectively removing may be regarded as adjusting the one or more ion mill operating characteristics to remove a material, at a certain predetermined rate, relative to removal of another material at a different predetermined rate. As well, selectively removing may be regarded as removing a specific material. Non-selectively removing may be regarded as operating the ion mill with a certain set of operating parameters without having control over the rates of removal of the one or more materials. This may lead to non-uniform or uneven underlying surface.

According to some embodiments of the invention, the ion mill operating characteristics may be set such that for a given time period, the predetermined rate of removal of a first material is higher than that of a second material. After which, the ion mill characteristics may be adjusted and set to another set of values, for a time period during which the predetermined rate of removal of the second material is higher than that of the first material. It may also be possible for the predetermined rates of all materials to be removed to be substantially same. For the purposes of this disclosure, period of time and time period may be used interchangeably.

Figure 3:
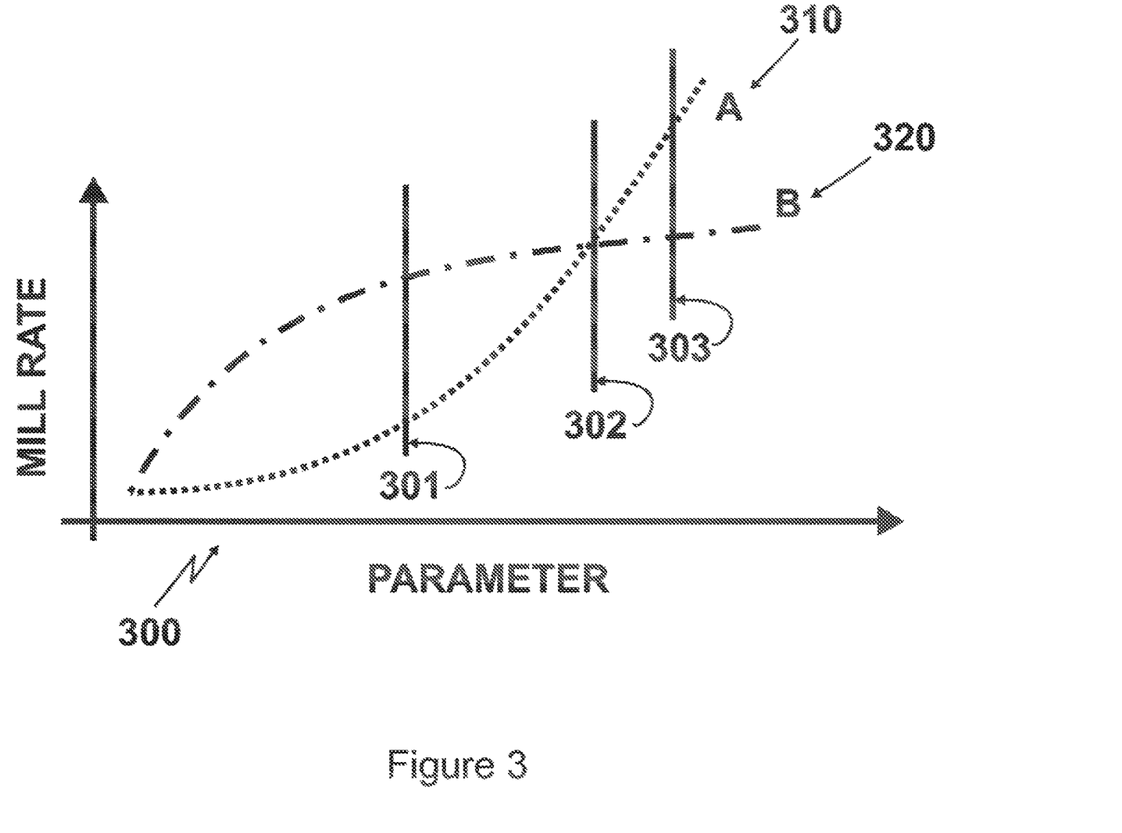
FIG. 3, in aspects, is a graph representing material mill rate versus an ion mill operating parameter for two materials A and B.

According to some embodiments of the invention, all but one of the one or more ion mill operating parameters may be set. One of the one or more ion mill operating parameters may be variable and the rate of removal of one or more materials for various values of the variable ion mill operating parameter may be obtained experimentally or via simulation. The results obtained and their respective ion mill operating parameters set to obtain them may be associated with each other and stored in a storage medium. A worker skilled in the art would readily understand the kind of storage medium needed. Based on the results obtained, a graph 300 may be plotted as shown in FIG. 3. The plotted graph shows mill rates or removal rates for two materials, A 310 and B 320, as a function of an ion mill operating parameter. At 301, the rate of removal for B is higher than the rate of removal for A. At 302, the rate of removal is substantially equal for both A and B and at 303, the rate of removal of A is higher than the rate of removal for B.

According to some embodiments of the invention, when encountered with a sample, for delayering, comprising materials A and B, the delayering may be set to take place with the one or more ion mill operating parameters set such that both material A and material B may be removed simultaneously. Simultaneous removal of A and B may be obtained when the one or more ion mill operating parameters are set such that the rates of removal for both A and B are substantially equal as seen at the intersection point 302. For example, the one or more ion mill operating parameters may be set such that material B is removed at a higher rate than material A. Thus selective removal of materials from a sample may be achieved. In such a delayering process, all but one of the ion mill operating parameters will stay constant for any rate of removal for the two materials A and B. The one ion mill operating parameter that is variable may be set to the respective value as required. For example, for delayering at 302, the required parameter value may be the parameter value corresponding to the intersection point. This would allow for both materials, A and B, to be removed at the same rate.

According to some embodiments of the invention, one or more ion mill operating characteristics may be set and the rate of removal as a function of sample stage angle, which may also be regarded as an operating parameter of the ion mill, may be determined. The determination of the rates of one or more materials may be experimental, or via simulation methods. Furthermore, any other ion mill operating characteristic may replace the sample stage angle.

Figure 4:
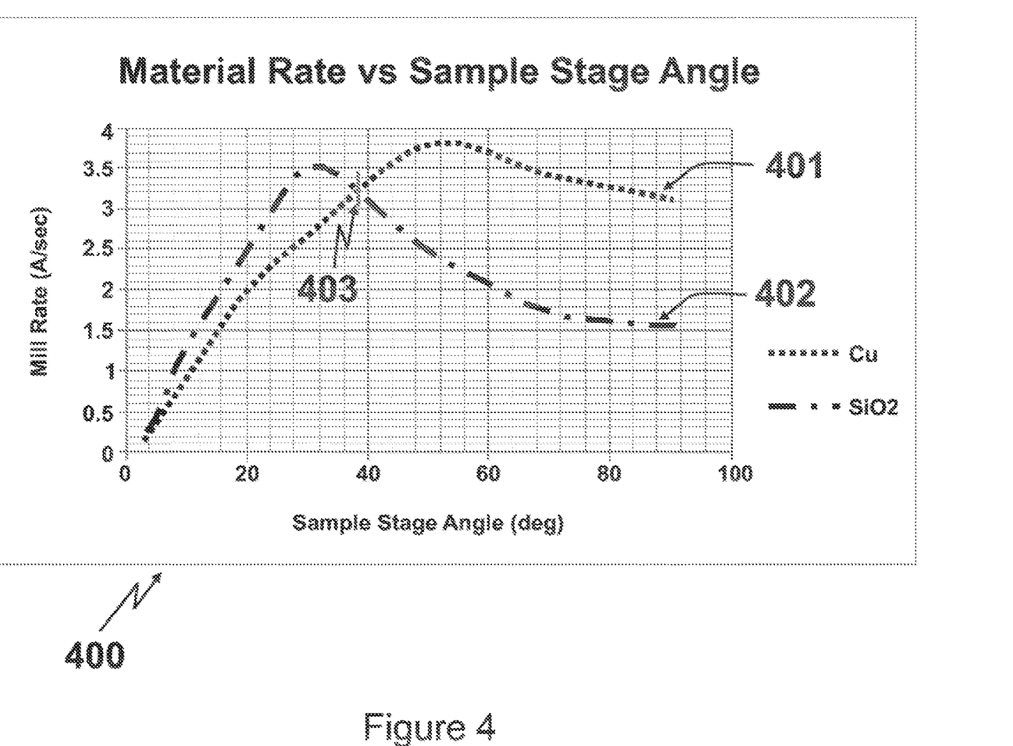
FIG. 4, in aspects, is a graph representing material mill rate versus sample stage angle for Copper (Cu) and Silicon Dioxide ($SiO_2$).

For example, the rates determined may be for two materials and the two materials may be Cu and $SiO_2$. The set of ion mill operating characteristics that relate to the rates of removal for Cu and $SiO_2$ for various sample stage angles may be associated with one another, respectively, and stored in any storage medium. Using the predetermined rates and the associated ion mill operating characteristics from the storage medium, a graph 400 comprising the predetermined rates as a function of sample stage angles may be plotted for both Cu 401 and $SiO_2$ 402. It is to be understood that delayering may be carried out without explicitly plotting a graph. For example, a control system that may comprise one or more processors may be able to control the ion mill to delayer a sample without explicitly plotting a graph.

Referring to the plotted graph 400 of FIG. 4, there may be an intersection point 403 obtained at which the rate of removal for both Cu and $SiO_2$ are substantially the same for a particular sample stage angle. The intersection point may provide the predetermined rate of removal for both Cu and $SiO_2$. For example, if a layer comprising Cu and $SiO_2$ is to be delayered, then the ion mill operating characteristics may be adjusted in accordance with the stored values, which may relate to the point of intersection, to remove both Cu and $SiO_2$ at the respective predetermined rate that would relate to the point of intersection for a period of time.

Figure 5:
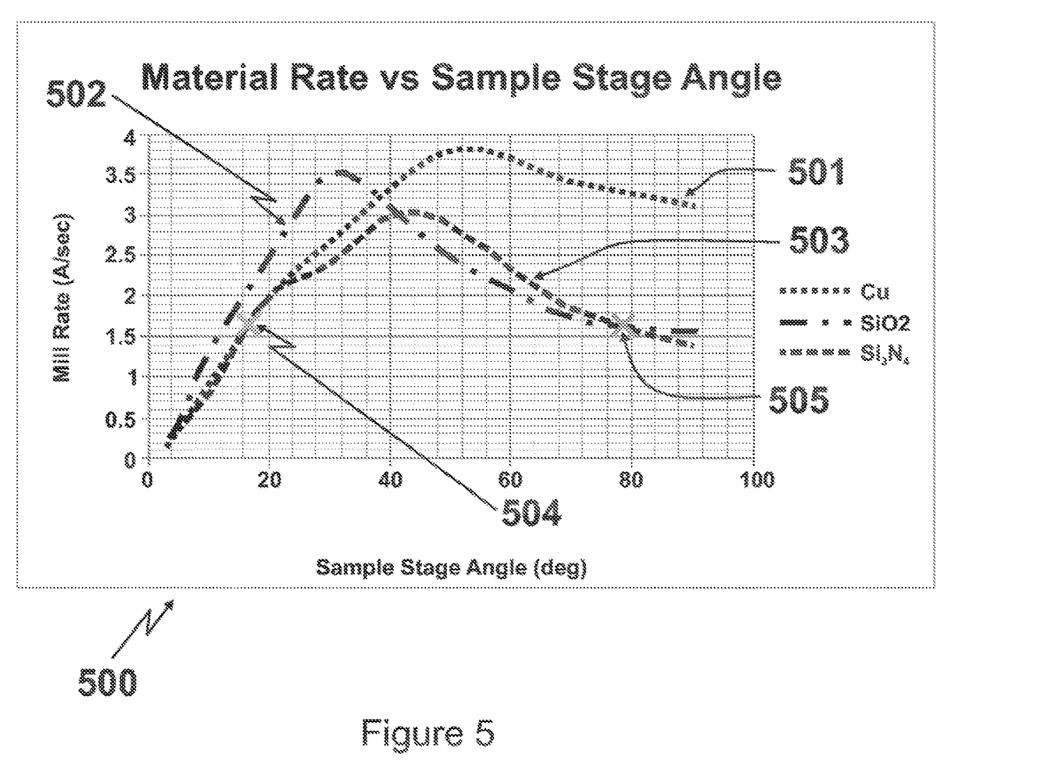
FIG. 5, in aspects, is a graph representing material mill rate versus sample stage angle for Copper (Cu), Silicon Dioxide ($SiO_2$) and Silicon Nitride ($Si_3N_4$).

As another example, the rates determined may be for three materials, which may be Cu, $SiO_2$ and $Si_3N_4$. The set of ion mill operating characteristics that relate to the rates of removal for Cu, $SiO_2$ and $Si_3N_4$ for various sample stage angles may be associated with one another, respectively, and stored in any storage medium as would be known to a worker skilled in the art. Using the predetermined rates and the associated ion mill operating characteristics from the storage medium, a graph 500 comprising the predetermined rates as a function of sample stage angles may be plotted for Cu 501, $SiO_2$ 502, and $Si_3N_4$ 503.

Referring to FIG. 5, from the plotted graph, an intersection point 504 can obtained at which the rate of removal for both Cu and $Si_3N_4$ are substantially the same for a particular sample stage angle. There may also be an intersection point 505, between $SiO_2$ and $Si_3N_4$, at which the rate of removal for both $SiO_2$ and $Si_3N_4$ may be substantially the same for a particular sample stage angle. For example, if a sample comprising a layer of Cu, $SiO_2$ and $Si_3N_4$ is to be delayered, then the ion mill operating characteristics may be adjusted, in accordance with the stored values that relate to the point of intersection for Cu and $Si_3N_4$, to selectively remove both Cu and $Si_3N_4$ at the respective predetermined rate, which would relate to the point of intersection for Cu and $Si_3N_4$, for a period of time. After which, the ion mill operating characteristics may be adjusted, in accordance with the stored values that relate to the point of intersection for $SiO_2$ and $Si_3N_4$, to selectively remove both $SiO_2$ and $Si_3N_4$ at the respective predetermined rate, which would relate to the point of intersection for $SiO_2$ and $Si_3N_4$, for a period of time, thus, leaving a substantially uniform underlying surface. The only ion mill operating parameter that may require change between the intersection points 504 and 505 might be the sample stage angle.

According to some embodiments of the invention, there may not be any intersection points between any of the materials that are to be removed. For instance, similar to the above example, there may be a layer that comprises three materials, A, B and C, to be delayered. After obtaining the predetermined rates and plotting a graph, similar to FIG. 5, it may be found that there may not be any intersection points. In such an instance, the ion mill operating characteristics may be set such that two of the three materials with lower predetermined rates may be selectively removed first for a period of time and subsequently the ion mill operating characteristics may be adjusted to selectively remove the third material with a higher predetermined rate for another period of time. The time period required for the removal of the first two materials may be higher than the time period required for the removal of the third material.

As an example, referring to the table below:

| | Predetermined Rate of removal- Material A (A/sec) | Predetermined Rate of removal- Material B (A/sec) | Predetermined Rate of removal- Material C (A/sec) |
|---|---|---|---|
| Ion mill operating Characteristics- Set I | 0.3 | 0.1 | 0.3 |
| Ion mill operating Characteristics- Set II | 0.1 | 0.3 | 0.1 |
| Ion mill operating Characteristics- Set III | 0.4 | 0.4 | 0.4 |

For a given ion mill operating characteristics—set III the predetermined rate at which all three materials A, B, and C may be removed is 0.4 A/sec. The ion mill operating characteristics may be adjusted to reflect the ion mill operating characteristics—set III for a certain period of time, wherein materials A, B, and C are all simultaneously removed. The underlying surface, after delayering the three materials A, B, and C simultaneously, would be substantially uniform. Similarly, the ion mill operating characteristics may be set to reflect the ion mill operating characteristics—set I for a period of time, for example $t_1$, wherein materials A and C are removed at 0.3 A/sec and material B is removed at 0.1 A/sec. After which, the ion mill operating characteristics may be set to reflect the ion mill operating characteristics—set II for a period of time, for example $t_2$, wherein materials A and C are removed at 0.1 A/sec and material B is removed at 0.3 A/sec. At $t=t_1+t_2$, all three materials A, B and C would have been removed equally thereby leaving the underlying surface substantially uniform.

According to some embodiments of the invention, there may be any number of materials. Selectively removing one or more materials leaves substantially uniform or even underlying surface. In addition, the selective removal of the one or more materials itself may be uniform or even. The selective removal of the one or more materials itself may also be non-uniform or uneven. Furthermore, regardless of the selective removal of the one or more materials being uniform or non-uniform, the underlying surface, after the removal of the one or more materials, is substantially uniform or even.

According to some embodiments of the invention, one or more operating characteristics or parameters may be adjusted to selectively remove a side-wall of a sample, wherein the side-wall comprises one or more materials. Predetermined rates, of one or more materials, and their respective associated ion mill operating characteristics may be relied upon to adjust the ion mill to selectively remove the one or more materials at respective predetermined rates from the side-wall of the sample. In addition, one or more materials surrounding a structure, in a sample, may be selectively removed at their respective predetermined rates by adjusting the one or more ion mill operating characteristics or parameters.

According to some embodiments of the invention, selective removal of material may take place until a certain thickness is removed. In aspects, sets of ion mill operating characteristics may be executed in a sequential manner to remove one or more materials. The time of execution for each set of ion mill operating characteristics may be random or may be set to be a certain value as may be determined previously through trial and error via experiments or simulation methods. In addition, the time of execution for each set of ion mill operating characteristics may be adjusted in real time by a control system. The control system may use a feedback mechanism to determine the optimal time of execution for each set of ion mill operating characteristics. The time of execution for each set of ion mill operating characteristics may be determined based on the thickness, of the one or more materials, to be removed.

Control System:

According to some embodiments of the invention, a system may comprise an ion mill in operative communication with a control system or one or more controllers. The control system may control the ion mill components individually or as a whole. The control system may comprise one or more processors with the appropriate software loaded into them to execute control. A worker skilled in the art would readily understand the necessary processors and associated software. The system comprising the ion mill in operative communication with the control system may also comprise mechanical, electronic and/or optical components for its working These may also be referred to as actuating elements. A worker skilled in the art would readily understand such mechanical, electronic and/or optical components. Furthermore, the control system may be programmed to control the system as a whole upon receiving input from a user.

According to some embodiments of the invention, the control system may comprise, a central control panel or board, at least one computer, processor/microprocessor, or central processing unit (CPU), along with associated computer software, one or more storage units/devices, power supplies, power converters, controllers, controller boards, various printed circuit boards (PCBs), for example, including input/output (I/O) and D/A (digital to analog) and A/D (analog to digital) functionalities, cables, wires, connectors, shielding, grounding, various electronic interfaces, and network connectors. The control system may be operatively connected and integrated with the ion mill and its various components.

The control system may further comprise one or more storage units to store predetermined information regarding removal rates for one or more materials and one or more ion mill operating characteristics or parameters. In addition, the stored information may be predetermined rates associated with their corresponding sets of ion mill operating parameters/characteristics for one or more materials. The predetermined rates may be obtained as explained in various aspects of the disclosure herein.

According to some embodiments of the invention, the control system may be used to operate the ion mill to perform delayering of a sample by entering appropriate inputs. The inputs may be provided to the control system via a control panel or any input device as would be readily known to a worker skilled in the art. The control system, upon receiving inputs, adjusts one or more ion mill operating characteristics to perform removal of one or more materials from a sample at their respective predetermined rates.

According to some embodiments of the invention, the input may include, but is not limited to the following: an individual value associated with just one ion mill operating parameter, one or more values associated with one or more ion mill operating parameters, the rate of removal of one or more materials, the delayering thickness or thickness of removal of one or more materials, the time period for removal of one or more materials, the one or more materials to be removed, sets of ion mill operating characteristics, execution time periods associated with one or more sets of ion mill operating characteristics, the sequence in which various sets of ion mill operating characteristics are to be executed, or any combinations thereof.

The control system may be programmed to automatically control one or more ion mill operating characteristics upon receiving an input from a user. For example, the input provided by a user may be to remove Cu from a sample for a certain period of time. Upon receiving this input from the user, the control system may, automatically, using the respective predetermined information associated with removal of Cu from a storage medium, adjust the one or more ion mill operating parameters to remove Cu for that period of time.

As another example, the user input may be to delayer a certain thickness of a sample. Upon receiving this input, the control system may automatically, using the relevant components of the delayering system, perform the following functions: detect the one or materials that may be present on the surface of the layer to be delayered, obtain the respective predetermined information associated with the removal of one or more materials from that layer, and adjust the one or more ion mill operating characteristics to delayer the sample to the desired thickness. One or more of the functions may be repeated until the specified thickness of the sample is delayered.

According to some embodiments of the invention, the control system may comprise a feedback system. The feedback system may be part of the entire system used for delayering a sample. The feedback system may use any detection mechanism to analyze, in real-time, the delayering of a sample. The detection mechanism may detect various facets of the delayering process as would be necessary to control the operation for optimal performance. A worker skilled in the art would readily know the various facets that need to be detected for optimization of the operation. The detected facets may be analyzed by the one or more processors. The analyzed results may then be used to automatically control one or more ion mill operating parameters or sets of operating parameters to optimally selectively delayer the sample. The detection mechanism may use a SIMS system. A worker skilled in the art would readily understand various detection mechanisms and detection systems/units.

Various Aspects of the Subject Matter Disclosed Herein:

In the instant application, there is further provided a method of de-layering ICs using an ion beam system, the ICs (or other sample) comprising of one or more materials, wherein rates of de-layering any of the one or more materials can be selectively controlled by adjusting one or more ion beam system parameters, the method comprising the steps of introducing an IC (or other sample) in a target path of an ion beam in the ion beam system, configuring the ion beam system to set each of the one or more parameters at respective predetermined levels that are associated with predetermined de-layering rates for each of the respective materials in the IC (or other sample); causing the ion beam gun to direct an ion beam at the IC (or other sample).

Other steps may include one or more of the following:
removing the IC (or other sample) after removal of a layer, analyzing the IC, repeating;
feedback control using a de-layered material detection element to assess progress of removal of layer or of detected materials in the sample to automatically and in real-time control selectivity or non-selectivity of material in any given layer or sample; and
removing substantially uniform layers comprising of homogeneous or non-homogeneous materials.

In some embodiments, there is also disclosed a method of determining relative de-layering rates of various materials using the system of the instant invention. The method comprises the steps of using the system described above to de-layer an known material and determine de-layering rates as a function of one or more parameters (including any interaction effects in respect of each of the one or more parameters and how interaction between each such parameter may impact said de-layering rates); repeating for one or more additional materials; optionally storing all such empirically gathered information in a data storage element for use by control system to automatically control selectivity levels of materials present in any given sample.

In another embodiment, there is provided an ion beam system for selectively de-layering ICs, the ICs comprising of one or more materials, the ion beam system comprising a chamber, one or more ion beam sources, and one or more a target stage. The system may optionally comprise additional elements to introduce various gases into the chamber, target stage control elements, and the following elements associated with any of the one or more ion beam sources: apertures, electrostatic lenses (condensors and objective); and all actuators necessary to adjust the one or more parameters.

Other components according to some embodiments of the invention may include one of more of the following:
Data storage component: for storing predetermined information regarding parameters and parameter effects on de-layering rates of materials;
Parameter actuator: various actuators on the ion beam system to automatically, in response to signals received from the control element, to adjust parameters;
Control element (e.g. a computer processor): the control element, based on predetermined information contained in the data storage component, and/or information received from the detection element, configured to send signals to the various parameter actuators to control adjustment of said parameters; and
De-layering material detection element (e.g. SIMS): this refers to a detection element capable of detecting or measuring changes in the sample that relate to de-layering or etching, such as the existence and quantity of different materials, the existence or physical, chemical or electrical characteristics of features on the sample as they become de-layered or material adjacent thereto becomes de-layered.

Some further aspects of the invention relate to the use of a broad beam ion milling system for de-layering layers of semiconductor die on a layer-by-layer basis, including through the methods and systems disclosed herein. Such aspects may include the use of an ion milling system to remove very thin layers of an IC to expose the underlying circuitry across the whole die. Each layer may be made up of a mixture of materials (metals and dielectrics) in varying shapes and structures.

The ion mill, according to some embodiments of the invention may consist of, for example, a large diameter gridded ion beam source and a variable angle cooled substrate stage that can be tilted and rotated, housed in a vacuum pumped process chamber. Various gas injection systems can deliver different process gasses, while a plasma bridge neutralizer is used to neutralize the ion beam. Vacuum gauges, a load-lock, vacuum pumps and computer complete the package. SIMS endpoint detection can be installed to help with accurately controlling the etch times.

Other de-layering material detection elements can be used and may include visual detection, other mass spectroscopy tools, or other chemical detection tools known to a worker skilled in the art.

The parameters of the use of the ion gun and associated target can be adjusted in order to control milling characteristics. Some of these parameters, which may affect the beam conditions, chamber conditions, sample conditions and orientation, and use of other materials in the beam or other material streams directed to the sample, can affect different milling characteristics. For example, by controlling the beam conditions (accelerating voltage, current), the gasses used (amount, type, and precisely where they are injected), the gun-to-sample angle, sample cooling and sample rotation speed, the milling characteristics of the semiconductor die materials may be controlled. Other parameters may include one or more of the following:

Chamber-base pressure, cross-over pressure, process pressure;
Load-lock base pressure, cross-over pressure;
Stage-linear location, angle, rotation speed, temperature;
Ion Source-RF power (fwd/reflected), accelerator voltage, accelerator current, beam voltage, beam current, extractor grid configuration (material, size, number and grid pattern of the extractor grids);
Plasma bridge neutralizer-cathode voltage, emission current;
Gas injection-PBN gas flow, source gas flows and types (could be multiple, could be inert or reactive), background gas flows and types (could be multiple);
Time-process step(s) time(s), number and order of steps (could use a series of different process conditions in a particular sequence);
Angle of the sample-to-gun (covers both moveable sample and moveable gun) is adjusted to select optimum etching rates and sidewall angle; and
Any of the parameters in known ion beam systems.

Selectivity (differential etch rate) between different materials used in the circuit layouts or other samples may depend on all, or some of those listed parameters and/or interaction effects therebetween. They can be adjusted and manipulated to allow selective etching (removing only a specific material type) or non-selective etching (removing all material at similar rates), allowing for accurate and precise removal of the homogenous and non-homogenous layers of an integrated circuit. The thickness of the removed layer, whether homogeneous or non-homogeneous, can therefore be made uniformly or substantially uniformly (and in any case significantly less than any stratum deposited in an IC).

The rate of removal for any given material as a function of one or more parameters can be predetermined and stored in a data storage component that is associated with systems and devices for carrying out the subject matter disclosed herein. This data may be collected based on empirical measurements that are systematically carried out by adjusting one or more parameters and then measuring de-layering rates for a particular material. By carrying out multi-factored analyses that assess de-layering rates relative to changes in various parameters, the interactive effects between such changes can also be predetermined and stored in the data storage component. Accordingly, the ion beam system can be configured to use the predetermined parameter de-layering parameter effects to carry out de-layering with a precise level of desired selectivity.

In some embodiments, the methods and systems disclosed herein are used to de-layer a target in a way that leverages the ability to selectively remove or etch layers that comprise multiple materials and are non-homogeneous. One application of this use is to provide for greater ease of visual and other types of analysis layer by layer. This is particularly useful in reverse engineering applications. While it may be an object to remove a layer of very uniform thickness across a non-homogenous target in order to analyze such layers underneath, it may also be an object to remove material surrounding a structure of a different material in order to more easily analyze (visually, electrically or otherwise) a particular material within a given layer. In other examples, the systems and methods disclosed herein may be used for deposition of materials onto the target to protect or pre-process that layer so that analysis or reverse engineering for a given layer is made possible. For example, once sufficient layers have been removed for analysis of a particular layer, it may be necessary to protect a layer from ambient conditions outside the ion beam chamber, and to expose the target for subsequent analysis of a particular layer. In other cases, material in a given layer may be pre-processed in order to make it more amenable to (a) etching at rates similar to other materials in the given layer that is non-homogeneous including etching using ion beam mill or other types of etching known in the art; and/or (b) analysis, visual or otherwise (for example, the surface characteristics of one material in a particular structure may be roughened or have material adsorbed or absorbed thereto to facilitate analysis). All of these objectives can be selectively managed and controlled by controlling the various parameters according to the systems and methods disclosed herein.

According to another embodiment, the parameters are controlled to manage the relative side-wall etching rates versus the de-layering etching rates. This may include, in some aspects, minimizing sidewall etching in a direction perpendicular to the direction of delayering.

The various parameters can also be used to control reaction rates selectively with various materials present on a sample when reactive species are introduced into the chamber and/or used as or mixed with the matter ejected from the ion beam source. Other objectives that can be achieved by controlling the parameters include the changes to surface roughness, chemical damage/modification, and physical damage/modification.

Some embodiments of the systems and methods described herein are configured to etch, deposit, or pre-process material from a sample uniformly across samples, even when the sample is large or very large, relative to the depth of the beam effect.

The parameters can be adjusted to selectively remove certain materials at different rate relative to other material that may be found in a given layer, so as to remove some materials and not others. Alternatively, the parameters can be adjusted to ensure substantially equal rates of de-layering to evenly remove extremely thin layers across large areas (in particular where the thickness of the layer removed is much smaller than the length or width of the sample in the plane of the layer). In some applications, the length and/or width may be in the range of 5-20 centimeters and the thickness of the removed layer may be in the range of picometers to nanometers.

Control system using feedback control of the SIMS measurement to determine rate of delayering and presence of de-layered material, or changes thereof. This can be used as part of a feedback control system to cause de-layering of desired materials at desired rates.

Exemplary Embodiments

Vacuum System:

Appropriately sized vacuum chamber to support automatic sample load/unload through an isolation lock. Accommodating the sample stage, ion-source, pumping ports, gas supply ports and ancillary viewing and monitoring features.

Fast pumping capability supporting process pressures in the 5e −4 regime with a leak rate less than 5e-5 torr l/s.

Sample Stage:

Capable of accepting a 4" diameter sample. Temperature controlled (cooled) to allow constant temperature operation. Thermal conduction from sample to stage. Rotation of sample about the central axis, and tilting in the plane of the ion-source from normal (+/−90 deg) to 0 degrees.

Shutter control protection of the sample during run-up and process-setting changes.

Ion Source:

12 cm diameter RF ICP auto impedance-matched with dual-grid focused output. Control of accelerating voltage, extraction voltage and beam current in the range of about 0-1000V, 0-500mA.

Gas Supply:

MFC controlled ion-source supply of noble or reactive gas and chamber background gas for chemical-mill enhancement. Also supply for PBN.

PBN:

Argon supplied ionizer injecting an electron stream for ion-beam neutralization.

De-Layering:

Every surface factor affects the milling process—material, topography, roughness, feature width, spacing, and the influence is dynamic in nature. The instant ion beam milling system is configured to match material rates as much as possible, and deal with feature topography through multiple beam angle/current application steps. One way to de-convolve all of these different effects from adjustments to parameters is to monitor effects by "trial and error" as much as predictable rate matching.

Another difficulty is to know where in the vertical structure the process is at any given time. A "material monitor" can be used to determine variations in the material mix and capturing new materials as they are uncovered—i.e. endpoint detection. A SIMS detector can be configured to be a "material monitor".

Another tool for influencing etch rates/selectivity is the use of additional or substitutional gasses either directly in the ion-source (reactive), or as a background gas fragmented by the ion-beam then able to selectively react on the surface.

Each step of the method disclosed herein may be executed on any computing device, such as a personal computer, server, PDA, or the like and pursuant to one or more, or a part of one or more, program elements, modules or objects generated from any programming language, such as C++, Java, C, or the like. In addition, each step, or a file or object or the like implementing each said step, may be executed by special purpose hardware or a circuit designed for that purpose.

We claim:

1. A system for reverse engineering a sample, the system comprising:
   an ion beam mill;
   a control system in operative communication with the ion beam mill to operate the ion beam mill, for each exposed surface of the sample, in accordance with two or more predetermined operational characteristics that correspond with a substantially identical ion beam mill removal rate for each of a plurality of materials identified in the exposed surface;
   wherein the control system is configured to, in accordance with said two or more predetermined operational characteristics simultaneously remove, using an ion beam from the ion beam mill, each of the plurality of materials at said substantially identical ion beam mill removal rate to remove a substantially planar layer of substantially constant thickness from the exposed surface of the sample to expose a newly exposed surface of the sample, whereby acquisition of surface data from each said newly exposed surface of the sample is used for reverse engineering at least a portion of the sample;
   wherein the predetermined operational characteristics are any of the following: angle of sample-to-ion beam direction, ion beam size, ion type, sample stage temperature, chamber base pressure, chamber cross-over pressure, chamber process pressure, sample stage linear location, sample stage angle, sample stage rotation speed, ion source accelerator voltage, ion source accelerator current, ion source beam voltage, ion source beam current, ion source extractor grid configuration, ion source extractor grid material, ion source RF power, extraction voltage, plasma bridge neutralizer (PBN) cathode voltage, PBN emission current, PBN gas flow, ion source type, ion source gas flow rate, chamber background gas type, chamber background gas flow rate, and sidewall angle.

2. The system of claim 1, wherein the ion beam operates in the presence of a reactive gas.

3. The system of claim 1, wherein the ion beam operates in the presence of a non-reactive gas.

4. The system of claim 2, wherein the predetermined operational characteristics further comprise any of: a type of reactive gas, and a flow rate of reactive gas.

5. The system of claim 2, further comprising a sample representation acquisition system operable to acquire the surface data from each said newly exposed surface.

6. The system of claim 5, wherein said sample representation acquisition system comprises an imaging system.

7. The system of claim 2, wherein the sample is reverse engineered by producing hierarchical circuit schematics from said surface data.

8. The system of claim 2, wherein said ion beam mill is one of a broad ion beam mill and a focused ion beam mill.

9. The system of claim 2, wherein said exposed surface is in the range of 5 to 20 square centimeters.

10. The system of claim 2, further comprising a data storage medium accessible by said control system to store said two or more predetermined operational characteristics therein to be accessed therefrom.

11. The system of claim 10, wherein the storage medium is one of an electronic and an optical storage medium.

12. The system of claim 2, wherein a thickness of said substantially planar layer is smaller than a length or width of said substantially planar layer.

* * * * *